(12) United States Patent
Suzuki et al.

(10) Patent No.: US 10,175,132 B2
(45) Date of Patent: Jan. 8, 2019

(54) PRESSURE SENSOR, DIFFERENTIAL PRESSURE SENSOR, AND MASS FLOW RATE CONTROL DEVICE USING SAME

(71) Applicant: Hitachi Metals, Ltd., Minato-ku, Tokyo (JP)

(72) Inventors: Kengo Suzuki, Tokyo (JP); Isao Sakaguchi, Mie-gun (JP); Takahiro Umeyama, Mie-gun (JP)

(73) Assignee: Hitachi Metals, Ltd., Tokyo (JP)

( * ) Notice: Subject to any disclaimer, the term of this patent is extended or adjusted under 35 U.S.C. 154(b) by 44 days.

(21) Appl. No.: 15/517,261

(22) PCT Filed: Oct. 6, 2015

(86) PCT No.: PCT/JP2015/078358
§ 371 (c)(1),
(2) Date: Apr. 6, 2017

(87) PCT Pub. No.: WO2016/056555
PCT Pub. Date: Apr. 14, 2016

(65) Prior Publication Data
US 2017/0299456 A1     Oct. 19, 2017

(30) Foreign Application Priority Data
Oct. 7, 2014   (JP) .................................. 2014-206347

(51) Int. Cl.
*G06F 11/00* (2006.01)
*G01L 19/02* (2006.01)
(Continued)

(52) U.S. Cl.
CPC ............ *G01L 19/02* (2013.01); *A61B 5/0008* (2013.01); *G01L 1/205* (2013.01); *G01L 1/22* (2013.01);
(Continued)

(58) Field of Classification Search
CPC ............... A61L 31/16; A61L 2300/404; A61L 2300/416; A61L 2300/432
(Continued)

(56) References Cited

U.S. PATENT DOCUMENTS

| 6,655,216 B1 | 12/2003 | Aizawa | |
|---|---|---|---|
| 2004/0210404 A1* | 10/2004 | Gysling | G01F 1/704 |
| | | | 702/50 |

(Continued)

FOREIGN PATENT DOCUMENTS

| JP | 63-217671 A | 9/1988 |
|---|---|---|
| JP | 64-26117 A | 1/1989 |

(Continued)

OTHER PUBLICATIONS

International Search Report (PCT/ISA/210) issued in PCT Application No. PCT/JP2015/078358 dated Dec. 28, 2015 with English-language translation (four (4) pages).

(Continued)

*Primary Examiner* — Edward Raymond
(74) *Attorney, Agent, or Firm* — Crowell & Moring LLP

(57) ABSTRACT

The present invention makes it possible to, even when a stainless steel is adopted in a diaphragm: prevent the diaphragm and a strain sensor from exfoliating from each other; be hardly susceptible to the influence of temperature in an operating environment; not allow the sensitivity of a pressure sensor to be dominated only by the mechanical characteristic of a material constituting the diaphragm; and increase the degree of freedom in design of members constituting the pressure sensor. A pressure sensor according to the present invention is, in order to solve the above problems, characterized in that: the pressure sensor has a diaphragm deforming by the pressure of a fluid, an elastic body covering the whole surface of the diaphragm and (Continued)

joining to the diaphragm on one side, and a strain sensor being arranged by joining on the other side of the elastic body and on an end side apart from a position corresponding to the center of the diaphragm and detecting the deformation of the elastic body working together with the deformation of the diaphragm as a strain; and the elastic body is formed of a material having a linear expansion coefficient close to the linear expansion coefficient of a material constituting the strain sensor.

20 Claims, 8 Drawing Sheets

(51) Int. Cl.

| | |
|---|---|
| *G01L 9/04* | (2006.01) |
| *G01L 13/02* | (2006.01) |
| *A61B 5/00* | (2006.01) |
| *G01L 1/20* | (2006.01) |
| *G01L 1/22* | (2006.01) |
| *G01L 9/12* | (2006.01) |
| *G01L 27/00* | (2006.01) |
| *A61B 5/021* | (2006.01) |
| *A61B 5/03* | (2006.01) |

(52) U.S. Cl.
CPC ............... *G01L 9/04* (2013.01); *G01L 9/125* (2013.01); *G01L 13/02* (2013.01); *G01L 27/007* (2013.01); *A61B 5/021* (2013.01); *A61B 5/03* (2013.01); *A61B 2562/0247* (2013.01); *A61B 2562/12* (2013.01)

(58) Field of Classification Search
USPC .................................. 702/138, 140, 182–185
See application file for complete search history.

(56) References Cited

U.S. PATENT DOCUMENTS

| | | | |
|---|---|---|---|
| 2005/0178208 A1 | 8/2005 | Benzel et al. | |
| 2010/0207754 A1* | 8/2010 | Shostak | ................ B60C 23/041 340/450 |
| 2014/0113828 A1* | 4/2014 | Gilbert | ................ H01L 39/126 505/100 |
| 2015/0141843 A1* | 5/2015 | Eberle | ................ A61B 5/02154 600/478 |

FOREIGN PATENT DOCUMENTS

| | | |
|---|---|---|
| JP | 6-35934 U | 5/1994 |
| JP | 7-12939 U | 3/1995 |
| JP | 2004-53344 A | 2/2004 |
| JP | 2005-227283 A | 8/2005 |
| KR | 10-2005-0103600 A | 11/2005 |
| KR | 10-2012-0015201 A | 2/2012 |

OTHER PUBLICATIONS

Japanese-language Written Opinion (PCT/ISA/237) issued in PCT Application No. PCT/JP2015/078358 dated Dec. 28, 2015 (three (3) pages).

Korean-language Office Action issued in counterpart Korean Application No. 10-2017-7009345 dated Aug. 21, 2018 with English translation (nine (9) pages).

* cited by examiner

PRESSURE SENSOR, DIFFERENTIAL PRESSURE SENSOR, AND MASS FLOW RATE CONTROL DEVICE USING SAME

TECHNICAL FIELD

The present invention relates: to a pressure sensor, a differential pressure sensor, and a mass flow controller using either of them; and in particular to a pressure sensor and a differential pressure sensor, those being suitable for detecting a pressure by making use of a deformation of a diaphragm accompanying pressurization, and a mass flow controller using either of the sensors.

BACKGROUND ART

As a pressure sensor which detects a pressure by making use of a deformation of a diaphragm accompanying pressurization, a pressure sensor which detects the deformation of a diaphragm accompanying pressurization as a strain by forming (attaching or the like) a strain gauge over the diaphragm is well known.

Such a strain gauge changes an electric resistance of itself even by a minimal deformation. Generally a method of measuring a differential voltage proportional to a pressure as an output by using four strain gauges as one set and constituting a bridge circuit is used well and a temperature characteristic of the strain gauges themselves can be compensated by constituting the bridge circuit. For example, even though strain gauges themselves have the temperature characteristic, the output of a strain sensor does not vary when the deformations of the four strain gauges caused by temperature variation are equal to each other.

Further, when the pressure of a measurement object is low and corrosion resistance is not required, a pressure sensor is used which is configured by forming a silicon diaphragm as a pressure receiving part by partially thinning a silicon substrate and forming strain gauges over the silicon diaphragm by impurity diffusion. A pressure sensor of such a configuration has the advantages that sensitivity is high and strain gauges can be formed as an integral structure over the silicon diaphragm and other advantages.

Such a pressure sensor however is not suitable when the pressure of the measurement object is high or when corrosion resistance is required and a pressure sensor configured by attaching strain gauges or attaching a strain sensor including strain gauges to a metal diaphragm is used frequently.

In Patent Literature 1, disclosed is a pressure sensor which is a micromachining type device for detecting a pressure value and includes two constituent components. More specifically, a first constituent component has a first diaphragm including a first material and a second constituent component including a second material has a first region and a second region. Further, the first region is thinner than the second region and the first diaphragm and at least a part of the first region are stiffly bonded to each other. Then in order to improve a type of a pressure sensor in which the first material has a thermal expansion coefficient larger than the second material, the first diaphragm including the first material is configured to transfer a horizontal inflation to the first region of the second constituent component with regard to temperature and the horizontal inflation is transferred through a first bonding material arranged between the first diaphragm and at least the part of the first region.

PRIOR ART DOCUMENTS

Patent Literatures

Patent Literature 1: Japanese Patent Application Laid-Open No. 2005-227283

SUMMARY OF INVENTION

Technical Problem

The problem to be solved by the present invention is classified roughly into two problems. That is, a first problem is a problem caused by difference in linear expansion coefficient between different types of materials and a second problem is a problem related to improvement of sensitivity of a pressure sensor.

Firstly, the first problem is explained as follows. A high corrosion resistant material such as a stainless steel has to be adopted to a part (diaphragm) directly in contact with a fluid in members constituting a pressure sensor in order to improve corrosion resistance of the pressure sensor having the configuration described above.

When silicon is adopted as the material of a strain sensor however, whereas the linear expansion coefficient of the silicon is $2.6 \times 10^{-6}$ $K^{-1}$, the linear expansion coefficient of a stainless steel is $15.9 \times 10^{-6}$ $K^{-1}$ and there is a big difference between them.

For that reason, if a silicon-made strain sensor is tried to be adhered to a stainless-steel-made diaphragm, a large dimensional difference is caused by temperature variation, hence the state of being adhered to each other cannot be retained, and troubles such as exfoliation and breakage of either the diaphragm or the strain sensor during the course of manufacturing are likely to occur.

Further, even when the adhesion between a silicon-made strain sensor and a stainless-steel-made diaphragm can be retained and breakage does not occur, a large stress is generated at an adhesive site because of the difference in linear expansion coefficient if temperature in an operating environment of a pressure sensor varies.

As a result, a strain sensor disadvantageously detects a strain even though the pressure of a fluid does not actually vary in a diaphragm and hence measurement error accompanying the variation of the temperature in an operating environment of a pressure sensor is caused.

Successively, the second problem is explained as follows. It is effective to reduce the elastic coefficient of a diaphragm and facilitate deformation in order to increase the sensitivity of a pressure sensor so as to be detectable even at a low pressure. That is, since the elastic coefficient of a diaphragm is determined by such as the Young's modulus of the material constituting the diaphragm and the diameter and thickness of a site which receives a pressure in the diaphragm, the elastic coefficient of the diaphragm can be reduced more by reducing the Young's modulus of the material constituting the diaphragm and also increasing the diameter and reducing the thickness of a site which receives a pressure.

When the elastic coefficient of a diaphragm is reduced and deformation is facilitated however, a principal stress that is generated during the deformation and added to a bend of the diaphragm increases and exceeds the elastic limit of the material and a pressure sensor cannot possibly be used continuously. That is, since the sensitivity of a pressure sensor and a principal stress added to a bend of a diaphragm are in the relationship of trade-off, the sensitivity of a pressure sensor is dominated by the mechanical characteristic of a material constituting a diaphragm as long as a single diaphragm is used as an elastic body.

The present invention has been established in view of the above situation and an object of the present invention is to provide: a pressure sensor and a differential pressure sensor which, even when a stainless steel is adopted in a diaphragm, can prevent the diaphragm and a strain sensor from exfoliating from each other, is hardly susceptible to the influence of temperature in an operating environment, does not allow the sensitivity of the pressure sensor to be dominated by only the mechanical characteristic of the material constituting the diaphragm, and can increase the degree of freedom in design of members constituting the pressure sensor; and a mass flow controller using the pressure sensor or the differential pressure sensor.

Solution to Problem

In order to solve the above problems, a pressure sensor according to the present invention is characterized in that: the pressure sensor has a diaphragm deforming by a pressure of a fluid, an elastic body covering the whole surface of the diaphragm and joining to the diaphragm on one side, and a strain sensor being arranged by joining on the other side of the elastic body and on an end side apart from a position corresponding to a center of the diaphragm and detecting a deformation of the elastic body working together with a deformation of the diaphragm as a strain, in which the elastic body is formed of a material having a linear expansion coefficient close to the linear expansion coefficient of a material constituting the strain sensor.

Further, a differential pressure sensor according to the present invention is, in order to solve the above problems, characterized in that: the differential pressure sensor has a first diaphragm and a second diaphragm, those being arranged so as to face each other and deforming by a pressure of a fluid, an elastic body being arranged between the first diaphragm and the second diaphragm and joining to the first diaphragm on one side and the second diaphragm on the other side, and a strain sensor being arranged on an end side apart from a position corresponding to a center of the first diaphragm and the second diaphragm on one side or the other side of the elastic body and detecting a deformation of the elastic body working together with a deformation of the first diaphragm and the second diaphragm as a strain, in which the elastic body is formed of a material having a linear expansion coefficient close to the linear expansion coefficient of a material constituting the strain sensor.

Advantageous Effects of Invention

The present invention makes it possible to prevent the diaphragm and a strain sensor from exfoliating from each other; be hardly susceptible to the influence of temperature in an operating environment; not to allow the sensitivity of a pressure sensor to be dominated only by the mechanical characteristic of a material constituting the diaphragm; and to increase the degree of freedom in design of members constituting the pressure sensor, even when a stainless steel is adopted in a diaphragm.

DESCRIPTION OF EMBODIMENTS

A pressure sensor, a differential pressure sensor, and a mass flow controller using either of them according to the present invention are explained hereunder on the basis of the embodiments shown in the figures. Here, in the embodiments explained below, an identical reference sign is used for an identical constituent component.

First Embodiment

Figure 1:
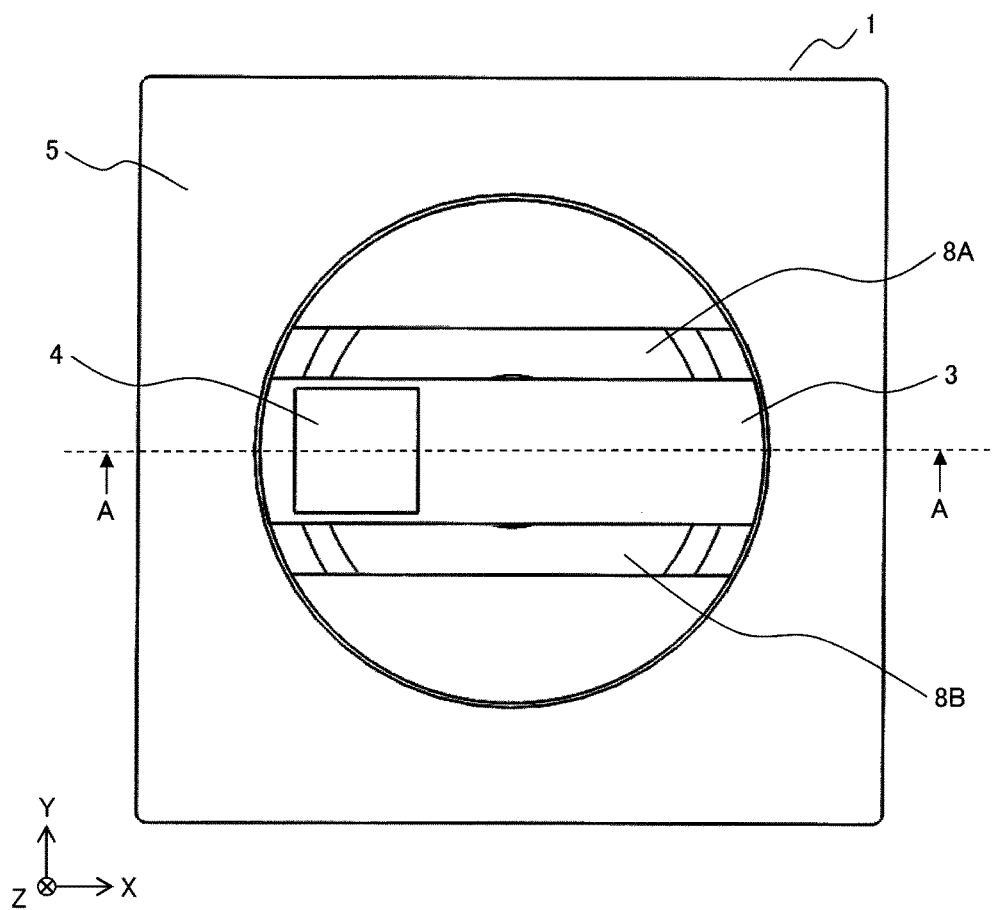
FIG. 1 is a plan view showing a first embodiment of a pressure sensor according to the present invention.
Figure 2:
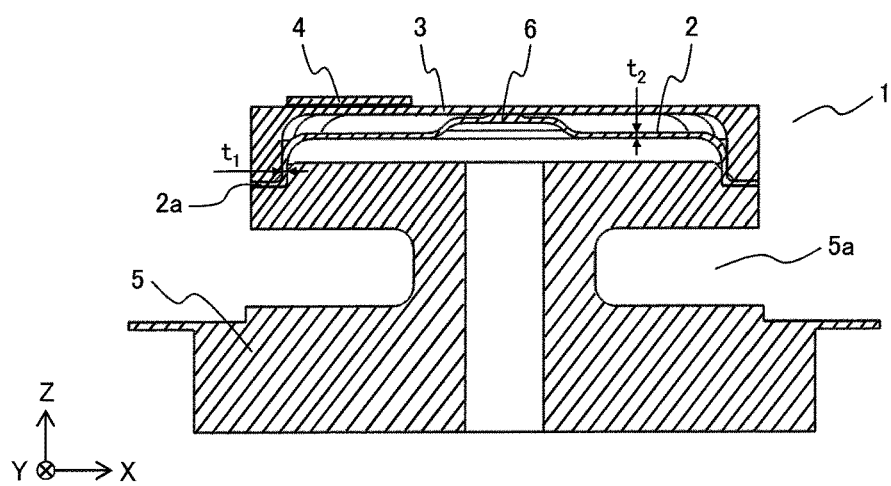
FIG. 2 is a sectional view taken on broken line A-A in FIG. 1.

A first embodiment of a pressure sensor according to the present invention is shown in FIGS. 1 and 2.

As shown in the figures, a pressure sensor 1 according to the present embodiment is generally configured by having: a diaphragm 2 deforming by the pressure of a fluid; an elastic body 3 covering the whole circumference of the diaphragm 2 and joining to the diaphragm 2 on one side; a strain sensor 4 being arranged by joining on the other side of the elastic body 3 and on an end side (left side in FIGS. 1 and 2) apart from a position corresponding to the center of the diaphragm 2 and detecting the deformation of the elastic body 3 working together with the deformation of the diaphragm 2 as a strain, the elastic body 3 formed of a material having a linear expansion coefficient close to the linear expansion coefficient of the material constituting the strain sensor 4; and a support 5 fixing an outer periphery of the diaphragm 2 and having a hole to introduce the fluid.

The elastic body 3 has a cylindrical shape and is configured so that: the center part may be thinner than the end part; slits 8A and 8B as holes may be formed at parts other than a part where the strain sensor 4 is arranged in the elastic body 3; and the slits 8A and 8B may extend from an end to the other end of the elastic body 3 in the manner of interposing the strain sensor 4 and may penetrate the elastic body 3 in the vertical direction (hereunder referred to as the Z direction) in FIG. 2.

More specifically, the diaphragm 2 according to the present embodiment is formed of a metal material and for example a stainless steel having a high corrosion resistance or a clad material including a stainless steel and another metal material is used as the material.

Meanwhile, the diaphragm 2 according to the present embodiment has a cylindrical shape and is configured so that: the thickness of the center part may be reduced so as to be thinner than the end part (t1>t2) by working; and the center of the thinner center part of the diaphragm 2 may bulge partially in order to join to the elastic body 3. Methods for thinning the center part of the diaphragm 2 are cutting, press working, and the like. The diaphragm 2 is structured so as to: deform by receiving the pressure of a fluid to be measured from the plane opposite to the plane where the strain sensor 4 is arranged; and generate a strain proportional to the pressure in the joined strain sensor 4.

Further, in the diaphragm 2 according to the present embodiment: the outer periphery is fixed to the support 5; and the diaphragm 2 and the support 5 are fixed so that airtightness may be secured by using resistance welding or laser welding and a fluid may not leak out through a gap between the diaphragm 2 and the support 5.

Meanwhile, the elastic body 3 is formed of a metal material and any one of a kovar alloy, a 42 alloy, and an invar alloy, those having a linear expansion coefficient close to silicon that is the material of the strain sensor 4, is used as the material for example. A material allowing the linear expansion coefficient of the elastic body 3 at 20° C. not to exceed 2.5 times the linear expansion coefficient of a semiconductor substrate (silicon) at 20° C. may also be used as the material.

Further, the elastic body 3 according to the present embodiment has a cylindrical shape and the thickness of the center part is reduced so as to be thinner than the end part by working. Since the elastic body 3 is not directly in contact with a fluid, it is possible to form a hole at a place other than a part where the strain sensor 4 is arranged with the aim of lowering stiffness. For example, it is possible to: form slits 8A and 8B linearly in the radial direction (hereunder referred to as the X direction) of the elastic body 3 on the sides of the strain sensor 4 in the manner of interposing the strain sensor 4; and thus form the part in which the strain sensor 4 is arranged into the shape of a beam. A fillet is formed at the thinner end part of the elastic body 3 and is structured so as to mitigate stress concentration accompanying pressurization or temperature variation.

Further, the elastic body 3: has a width equal to or larger than the size of the strain sensor 4 in order to make it possible to arrange the strain sensor 4; is fixed at least at two places of a joint 6 in the center of the diaphragm 2 and the outer periphery of the diaphragm 2 (the joint 6 is fixed at one point and the outer periphery is fixed at the whole periphery); and is fixed stiffly at the joint 6 by welding so as not to exfoliate by pressurization, the variation of temperature, or the like. The joint 6 mitigates the influence of a linear expansion coefficient difference between the diaphragm 2 and the elastic body 3 by being fixed not at the whole thin membrane part of the diaphragm 2 but only at a partial region (one point). Since the elastic body 3 is joined to the diaphragm 2 with the joint 6 interposed, a warp is caused in conjunction with the deformation of the diaphragm 2 but the elastic coefficient of the diaphragm 2 can be reinforced by appropriately designing the elastic coefficient of the elastic body 3.

The depth of the thin membrane part of the elastic body 3 is shallower than the height of the diaphragm 2 and the elastic body 3 and the diaphragm 2 push each other with the joint 6 interposed. By pushing each other, the elastic body 3 is pushed up in the manner of bulging and the diaphragm 2 is pushed down. By pushing the elastic body 3 up in the state of not applying pressure, the effects of inhibiting the concavity and convexity of the elastic body 3 from being reversed accompanying pressurization and improving the linearity of sensitivity can be obtained. Further, by pushing the diaphragm 2 down, a principal stress at the bottom plane end of the diaphragm 2 can be a compressive stress which is opposite to a stress generated when pressure is applied and the principal stress generated in the diaphragm 2 when the pressure is applied can be reduced.

Figure 3:
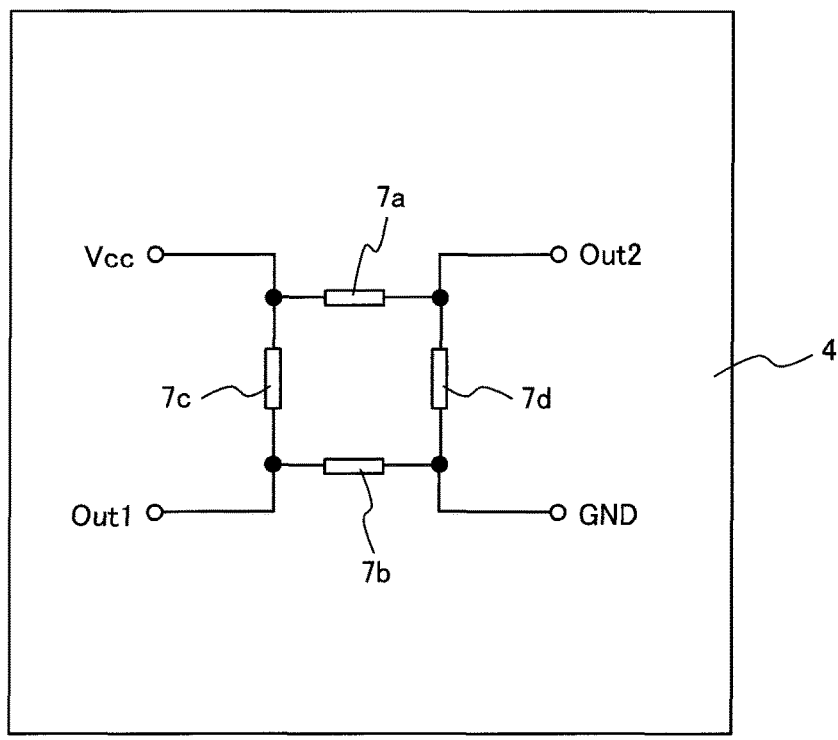
FIG. 3 shows a strain sensor adopted in a pressure sensor according to the present invention taking a bridge circuit including four strain gauges as an example.

Successively, the configuration of the strain sensor 4 is explained in reference to FIGS. 1 to 3. As shown in FIG. 3, strain gauges 7a, 7b, 7c, and 7d are formed in the surface center of the strain sensor 4 and a bridge circuit includes the four strain gauges. Further, the strain sensor 4 is manufactured with a monocrystal silicon substrate used as the material and the strain gauges 7a, 7b, 7c, and 7d are formed by diffusing impurities into the silicon substrate. Moreover, the strain gauges 7a and 7b are arranged so that the X direction may be parallel with the direction where electric current flows and the strain gauges 7c and 7d are arranged so that the radial direction of the diaphragm 2 (hereunder referred to as the Y direction) may be parallel with the direction where electric current flows.

By such a configuration of the strain sensor 4 as stated above, an output proportional to a strain difference between the X direction and the Y direction is obtained as a differential output (Out 1–Out 2) of intermediate potential of the bridge circuit. Meanwhile, with regard to the influence of temperature variation on the electric resistance of the strain gauges 7a, 7b, 7c, and 7d, the output of the strain sensor 4 is not affected because the variation of the electric resistance caused by temperature variation is also equalized as long as the temperature characteristics of the four strain gauges are identical.

For example, in the case of an elastic body 3 in which slits 8A and 8B are not formed, deformation caused by pressure is axisymmetric and strain difference between the X direction and the Y direction cannot be obtained when a strain sensor 4 is arranged in the center of a diaphragm 2. A strain sensor 4 is therefore arranged at the end of the thin membrane part of the elastic body 3 with the aim of improving sensitivity. The reason is that, by arranging a strain sensor 4 at the end of the thin membrane part of an elastic body 3, compressive strain and tensile strain are generated in the strain sensor 4 in the X direction and the Y direction respectively and the strain difference can be increased. As a result, the improvement of the sensitivity of a pressure sensor 1 can be expected.

Further, the elastic body 3 and the strain sensor 4 are fixed stiffly with a joining layer interposed. By using metal (Au/Sn or Au/Ge) junction or a low-melting-point glass (a vanadium-based glass) junction for the junction of the both, creep deformation accompanying long-term temperature variation and pressurization can be inhibited. The metal (Au/Sn or Au/Ge) and the low-melting-point glass (the vanadium-based glass) are hard materials and hence the deformation of an elastic body 3 can be transferred effectively to a strain sensor 4.

Further, the support 5 is a member to support the connection of a flange (not shown in the figures) attached to a pipe in which a fluid as a measurement object flows and the diaphragm 2. The flange and the pipe are fixed with a screw. If the flange and the diaphragm 2 are fixed directly, sensitivity may possibly change by the influence of the fastening by the screw. Hence a constriction 5a is formed at a part of the support 5 in order to mitigate a stress accompanying the fastening of the screw transferred from the bottom part of the support 5.

Further, as stated above, the slits 8A and 8B are formed in the elastic body 3 and penetrate the elastic body 3 in the Z direction. The slits 8A and 8B are formed from an end to the other end of the elastic body 3 in terms of length and arranged at places apart from the strain sensor 4 at a certain distance in terms of location in the X direction in FIG. 1. The elastic body 3 in which the strain sensor 4 is arranged has the shape of a beam and the center and both the ends are fixed to the diaphragm 2.

For example, in the case of a pressure sensor 1 not having slits 8A and 8B in an elastic body 3, an output is caused by temperature variation in a strain sensor 4 fixed to an end of the elastic body 3. This is because the linear expansion coefficient of a stainless steel that is the material of a diaphragm 2 is not less than five times the linear expansion coefficient of silicon that is the material of the strain sensor 4 and there is a difference. Further, the influence of the following fact is also large. The fact is that a joining layer for transferring the deformation of the elastic body 3 effectively to the strain sensor 4 is formed of Au/Sn or Au/Ge or a low-melting-point glass (a vanadium-based glass), those being hard materials.

When the temperature of the exterior of the pressure sensor 1 drops, compressive strain is generated in the strain sensor 4 in both the X direction and the Y direction. Although an output does not change as long as the strains in the X direction and the Y direction are equal, since the compressive strain in the Y direction is larger, the output changes. This is because the stress is mitigated by the deformation of the elastic body 3 in the X direction but, in the Y direction, the stress is mitigated less than in the X direction since the elastic body 3 has a small area and hardly deforms.

Further, since junction of low-melting-point glass or the like at a high temperature of not lower than 300° C. is used for fixing the elastic body 3 and the strain sensor 4, when the temperature lowers after the junction, a strain difference is generated between the X direction and the Y direction and is detected as an output offset at an initial zero point. If the output offset at the initial zero point is generated, following problems arise: a circuit for correcting the offset to zero is required; the range in which the pressure sensor 1 can be used reduces; and others. Further, when the pressure sensor 1 is used, temperature varies by about 100° C. in a consumer pressure sensor and about 160° C. in an in-car pressure sensor and the zero point output of the pressure sensor 1 varies.

In order to improve the above problems therefore, by forming a slit or the like in the elastic body 3, the elastic body 3 can deform easily also in the Y direction and a compressive strain applied to the strain sensor 4 in the Y direction reduces. As a result, strain difference between the X direction and the Y direction reduces and the output variation at zero point accompanying temperature variation can be suppressed. As a means for mitigating a compressive strain applied to the strain sensor 4 in the Y direction, the linear slits 8A and 8B are formed in the elastic body 3 in the present embodiment.

The depth of the thin membrane part of the elastic body 3 is shallower than the height of the diaphragm 2 and the elastic body 3 and the diaphragm 2 push each other with the joint 6 interposed. By pushing each other, the elastic body 3 protrudes to form a convex shape toward the plane in which the strain sensor 4 is arranged at least from a flat plane. Because the elastic body 3 has a convex shape, the concavity and convexity of the elastic body 3 is prevented from being reversed in response to pressurization by a fluid. In this way, buckling and sign inversion of the strain sensor 4 caused by the reverse of the concavity and convexity of the elastic body 3 are prevented and the improvement in the linearity of sensitivity is intended.

Further, as stated above, the diaphragm 2 is formed of a metal material, a stainless steel having a high corrosion resistance is used as the material, and the diaphragm 2 has a cylindrical shape and is configured so that: the thickness of the center part may be reduced so as to be thinner than the end part by working; and the center of the thinner center part of the diaphragm 2 may bulge partially in order to join to the elastic body 3. Press working is used as a method of forming the diaphragm 2, a brim 2a for welding with the support 5 is provided at the outer periphery of the diaphragm 2, and a fluid is prevented from leaking by welding the brim 2a of the diaphragm 2 with the support 5. No bend exists between the outer periphery and the center part of the diaphragm 2 and deformation caused when pressure is applied by a fluid is larger and sensitivity also increases in comparison with the case where a bend exists.

When pressure is applied by a fluid, the diaphragm 2 is pushed up by the fluid and a maximum principal stress is generated at an end on the bottom plane of the diaphragm 2. Since the maximum principal tensile stress should not exceed the proof stress of the material of the diaphragm 2, the diaphragm 2 is structured so as to be pushed down by the elastic body 3 in the state of applying no pressure. By pushing the diaphragm 2 down, a compressive stress is generated at the end on the bottom plane of the diaphragm 2 in the state of applying no pressure. The stress is a stress opposite to a stress generated when pressure is applied, hence can reduce the principal stress applied to the diaphragm 2, and expands the dynamic range of the pressure.

By such a configuration according to the present embodiment, the movable part of the pressure sensor 1 is formed of two parts of the elastic body 3 and the diaphragm 2 and materials most suitable for a plurality of functions required for respective members can be selected independently; for example, a part which is required to adopt a material of a high corrosion resistance because it is directly in contact with a fluid includes the diaphragm 2 formed of a stainless steel or the like, and a part which requires a low linear expansion coefficient from the necessity of joining to the strain sensor 4 includes the elastic body 3 formed of any one of a kovar alloy, a 42 alloy, and an invar alloy.

As a result, since the difference between the linear thermal expansion coefficient of the strain sensor 4 and the linear thermal expansion coefficient of the elastic body 3 where the strain sensor 4 is arranged can be reduced while a high corrosion resistance against a fluid is retained, the first problem described above on exfoliation and temperature in operating environment can be solved.

Meanwhile, in the above configuration, by joining the respective surfaces of the diaphragm 2 and the elastic body 3 designed individually, the deformation of the diaphragm 2 that has received the pressure of a fluid can be transferred to the elastic body 3 where the strain sensor 4 is arranged.

As a result, a plurality of such joined members are integrated and the function as the pressure sensor 1 can be exhibited. Here, even in the case of joining the diaphragm 2 formed of a stainless steel and the elastic body 3 formed of any one of a kovar alloy, a 42 alloy, and an invar alloy with a joint which is a welded part (weld) interposed for example, they are not joined in wide ranges but at most only parts of them are joined in small areas.

Even when difference in linear expansion coefficient exists between the diaphragm 2 and the elastic body 3 therefore, the concern of exfoliation due to the difference reduces in comparison with surface bonding in prior art. Likewise, also the magnitude of a tensile stress or a compressive stress generated in response to the difference in linear expansion coefficient caused by the variation of temperature in an operating environment reduces in comparison with a case of joining at large areas.

Further, according to the above configuration, by configuring the pressure sensor 1 with a plurality of members, the degree of freedom not only in the selection of materials but also in the design of the shapes and dimensions of the respective members increases in comparison with the case of configuring the pressure sensor 1 with a single member.

That is, when a movable part includes only the diaphragm 2, the elastic coefficient k of the movable part is determined by the Young's modulus and the shape of the diaphragm 2. On the other hand, when a movable part includes the diaphragm 2 and the elastic body 3, a member formed by joining them to each other operates as a whole as a movable part having an elastic coefficient equal to $k=k_1+k_2$ (here, $k_1$ is the elastic coefficient of the diaphragm 2 and $k_2$ is the elastic coefficient of the elastic body 3). As a result, for example, without largely changing a whole elastic coefficient k, it is possible to design the elastic coefficient $k_1$ of the diaphragm 2 so as to be smaller and the elastic coefficient $k_2$ of the elastic body 3 so as to be larger and the like and hence the degree of freedom in design increases.

Moreover, by separating a movable part into two parts of the diaphragm 2 and the elastic body 3 a structure of pushing the elastic body 3 up and pushing the diaphragm 2 down can be obtained, for example.

Further, when pressure is applied by a fluid, the diaphragm 2 is pushed up by the fluid, the maximum principal stress is generated at the end on the bottom plane of the diaphragm 2, and the maximum principal stress should not exceed the proof stress of the material constituting the diaphragm 2. Measures of adopting a structure for mitigating the maximum principal stress by increasing the curvature of the end on the bottom plane of the diaphragm 2 for example have heretofore been taken in order to secure a dynamic range of pressure. If the curvature of the end on the bottom plane of the diaphragm 2 is increased however, the deformation amount of the diaphragm itself reduces and sensitivity may deteriorate undesirably.

To cope with that, like the present embodiment, by adopting a structure of applying pressure to the diaphragm 2 and the elastic body 3 each other, the diaphragm 2 is pushed down, the principal stress at the end on the bottom plane of the diaphragm 2 in the initial state can be a compressive stress that is opposite to a stress generated when pressure is applied, the principal stress added to the diaphragm 2 can be reduced, and the range of pressure measurable by the pressure sensor can be expanded.

Further, in an existing diaphragm, the junction plane of a diaphragm has been depressed sometimes by the influence of processing accuracy or junction. Since a diaphragm bulges by the pressure applied by a fluid, the concavity and convexity of the diaphragm have been reversed by the pressurization. This also influences a strain sensor joined to the diaphragm and the strain added to the strain sensor reverses from tension to compression. There has been the possibility that, because of the reverse of the concavity and convexity in the diaphragm and the reverse of the tension and compression in the strain sensor, buckling of the diaphragm, sign inversion of the strain sensor, and the like are generated and non-linearity increases.

To cope with that, in the present embodiment, it is attempted to inhibit the reverse of the concavity and convexity of the elastic body 3 caused by pressurization and improve the linearity of sensitivity by pushing the elastic body 3 up from an initial state. By those measures, the second problem stated above can be solved.

In this way, by a configuration according to the present embodiment, even when a stainless steel is adopted in a diaphragm, the diaphragm and a strain sensor do not exfoliate from each other, temperature in an operating environment hardly exerts influence, the sensitivity of a pressure sensor is not dominated only by the mechanical characteristic of the material constituting the diaphragm, and the degree of freedom in the design of members constituting the pressure sensor can be increased.

Second Embodiment

Figure 4:
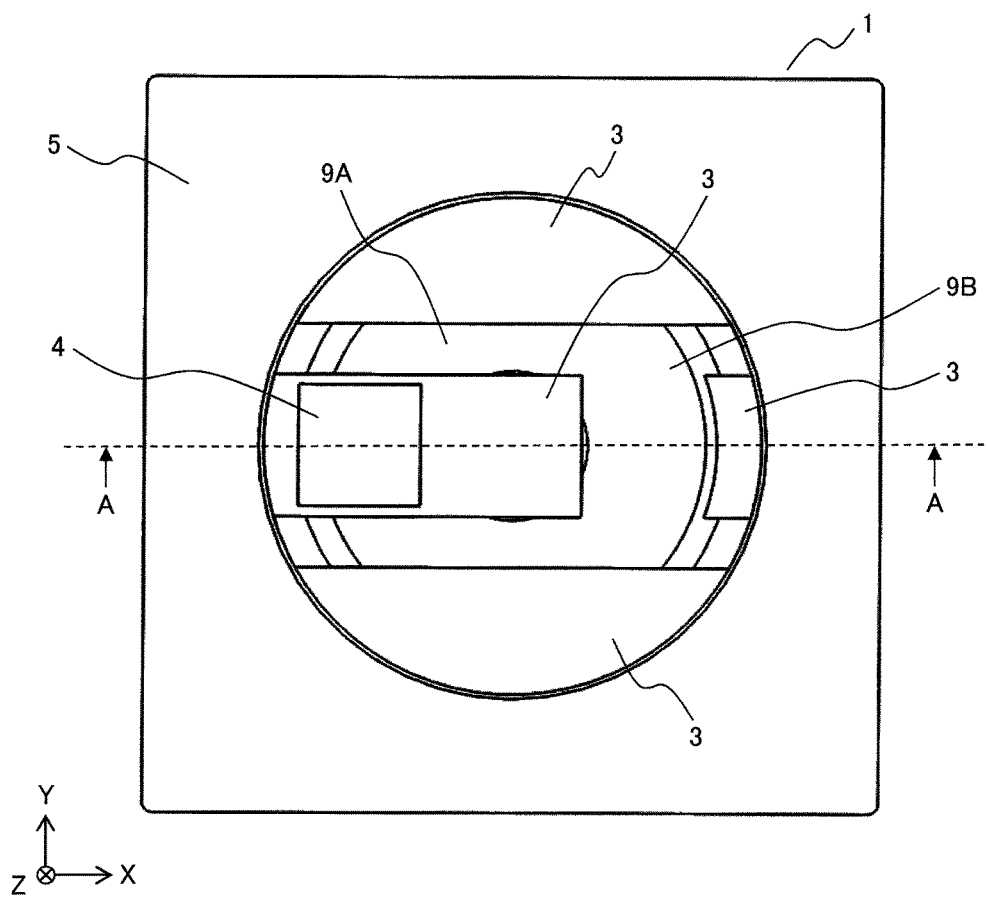
FIG. 4 is a plan view showing a second embodiment of a pressure sensor according to the present invention.
Figure 5:
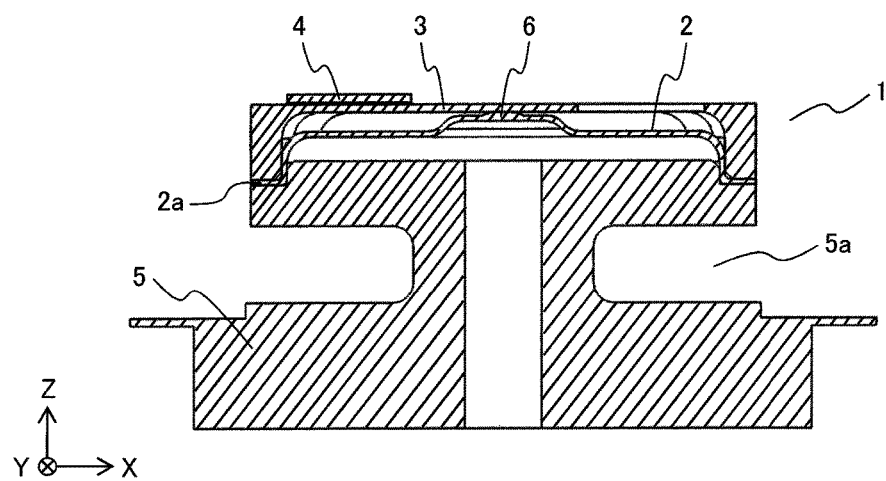
FIG. 5 is a sectional view taken on broken line A-A in FIG. 4.

A second embodiment of a pressure sensor according to the present invention is shown in FIGS. 4 and 5. In the second embodiment shown below, only points different from the first embodiment are explained.

In a pressure sensor 1 according to the present embodiment shown in the figures, at places other than the part where a strain sensor 4 is arranged in an elastic body 3, a first through hole 9A and a second through hole 9B are formed, the first through hole 9A penetrating the elastic body 3 in the Z direction in the manner of interposing the strain sensor 4, and the second through hole 9B communicating with the first through hole 9A and penetrating the elastic body 3 in the Z direction on the side other than the side where the strain sensor 4 is arranged.

That is, in the pressure sensor 1 according to the present embodiment: the first through hole 9A formed in the elastic body 3 at a place apart from the strain sensor 4 at a certain distance in the Y direction is formed from an end to the other end of the elastic body 3 in the X direction in length; and the second through hole 9B is formed in the elastic body 3, when viewed from a joint 6, on the side other than the side where the strain sensor 4 is arranged. The elastic body 3 over which the strain sensor 4 is arranged has the shape of a beam and is fixed to a diaphragm 2 only at the center and an end on the side where the strain sensor 4 is arranged.

By such a configuration according to the present embodiment, effects similar to the first embodiment can be obtained. In addition, since the number of the sites where the elastic body 3 is fixed is smaller than the first embodiment, the effects that the stiffness of the elastic body 3 reduces, the elastic body 3 deforms more than the first embodiment, and also sensitivity increases can be obtained.

Third Embodiment

Figure 6:
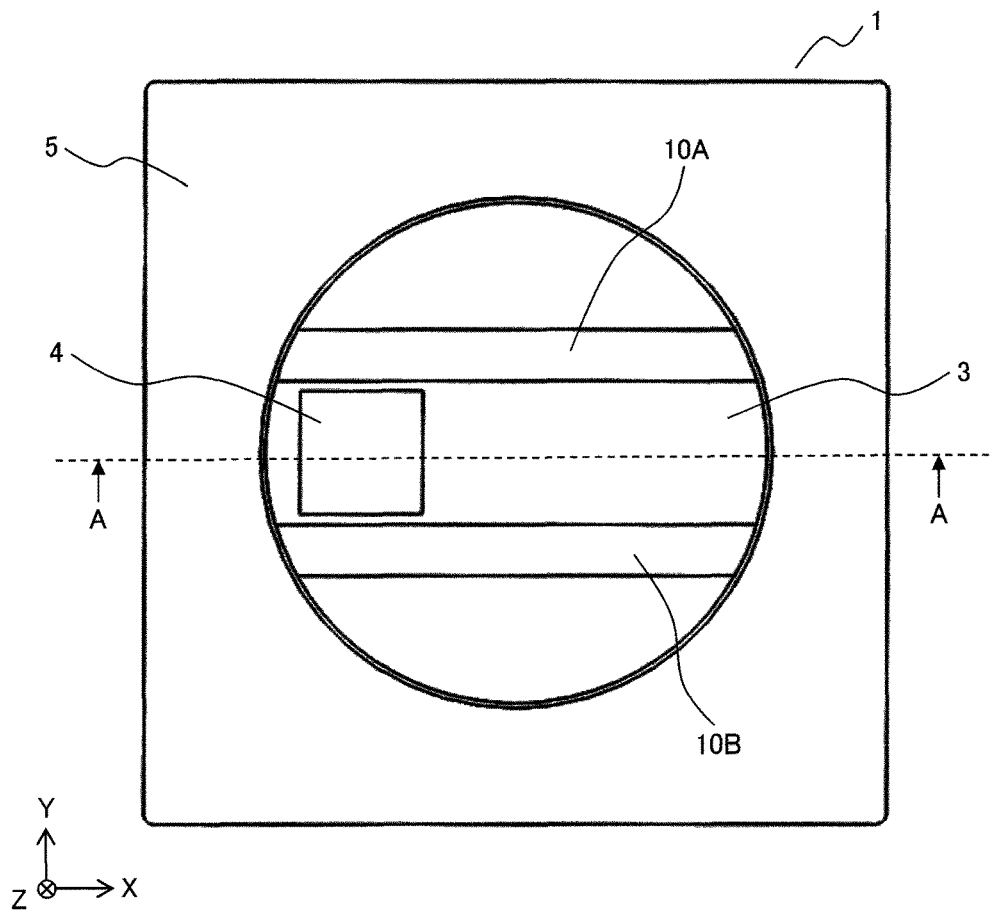
FIG. 6 is a plan view showing a third embodiment of a pressure sensor according to the present invention.
Figure 7:
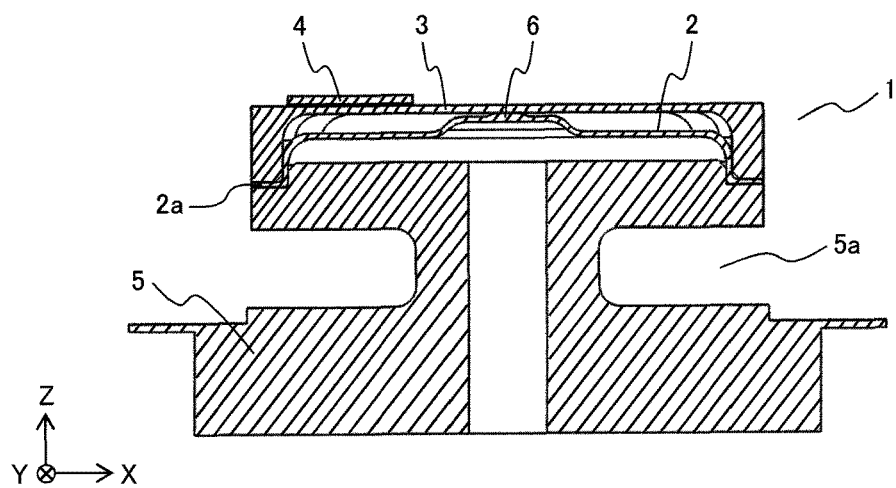
FIG. 7 is a sectional view taken on broken line A-A in FIG. 6.

A third embodiment of a pressure sensor according to the present invention is shown in FIGS. 6 and 7. In the third embodiment shown below, only points different from the first embodiment are explained.

A pressure sensor 1 according to the present embodiment shown in the figures has two recesses (concavities) 10A and 10B, those being formed in an elastic body 3 in the manner of interposing a strain sensor 4 and extending from an end to the other end of the elastic body 3, and the recesses (concavities) 10A and 10B are configured so as not to penetrate the elastic body 3.

That is, in the pressure sensor 1 according to the present embodiment, the recesses (concavities) 10A and 10B are formed from an end to the other end of the elastic body 3 in length in the X direction and are arranged at places apart from the strain sensor 4 at a certain distance. The elastic body 3 does not have the shape of a beam and hence the twist of a beam can be restrained even when a joint 6 displaces in the Y direction.

By such a configuration according to the present embodiment, effects similar to the first embodiment can be obtained. In addition, since the recesses (concavities) 10A and 10B do not penetrate the elastic body 3 in comparison with the first embodiment, a structure withstanding positional distortion caused by mounting error or processing error can be obtained although the deformation is small.

Fourth Embodiment

Figure 8:
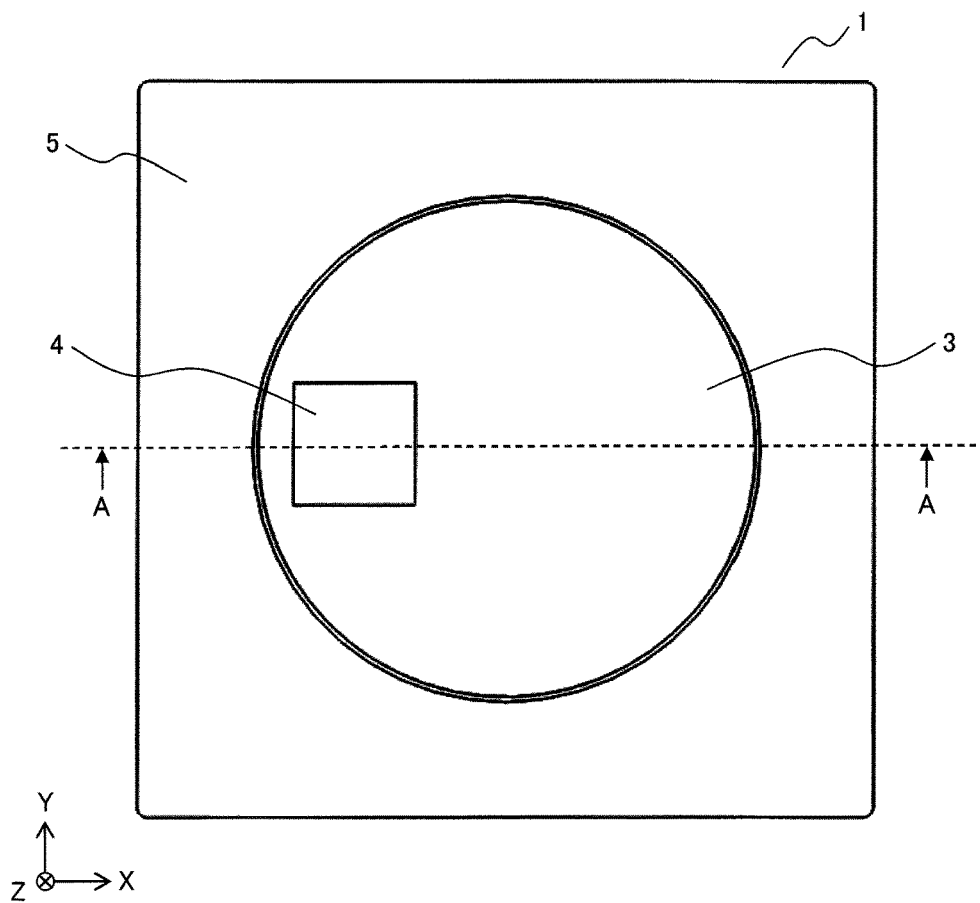
FIG. 8 is a plan view showing a fourth embodiment of a pressure sensor according to the present invention.
Figure 9:
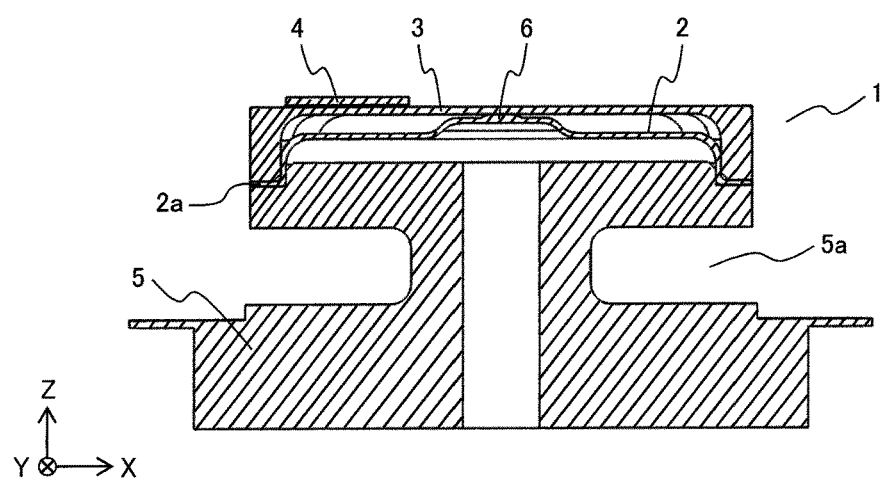
FIG. 9 is a sectional view taken on broken line A-A in FIG. 8.

A fourth embodiment of a pressure sensor according to the present invention is shown in FIGS. 8 and 9. In the fourth embodiment shown below, only points different from the first embodiment are explained.

In a pressure sensor 1 according to the present embodiment shown in the figures, only a strain sensor 4 is arranged over the surface of an elastic body 3 and processing such as slitting is not applied.

By such a configuration according to the present embodiment, not only effects similar to the first embodiment can be obtained but also the pressure sensor 1 can withstand positional distortion caused by mounting error or processing error and the processing cost can be reduced although the deformation is smaller than the first embodiment.

Fifth Embodiment

Figure 10:
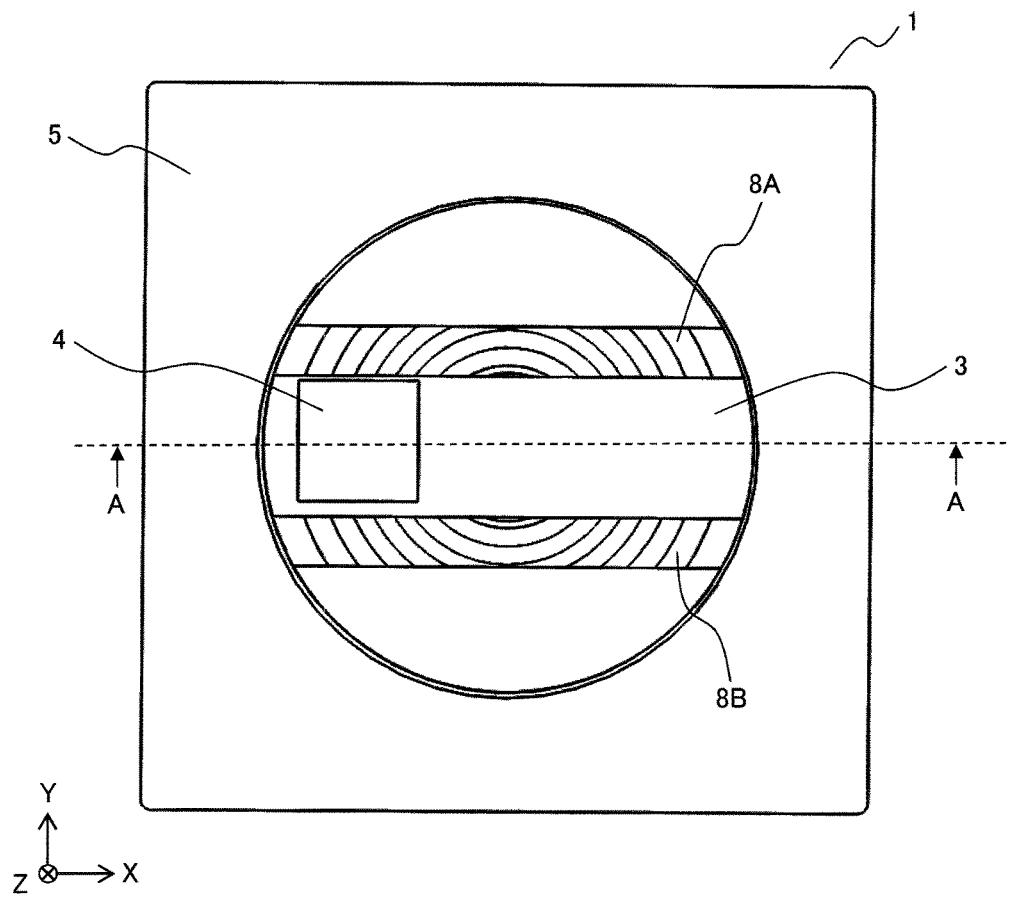
FIG. 10 is a plan view showing a fifth embodiment of a pressure sensor according to the present invention.
Figure 11:
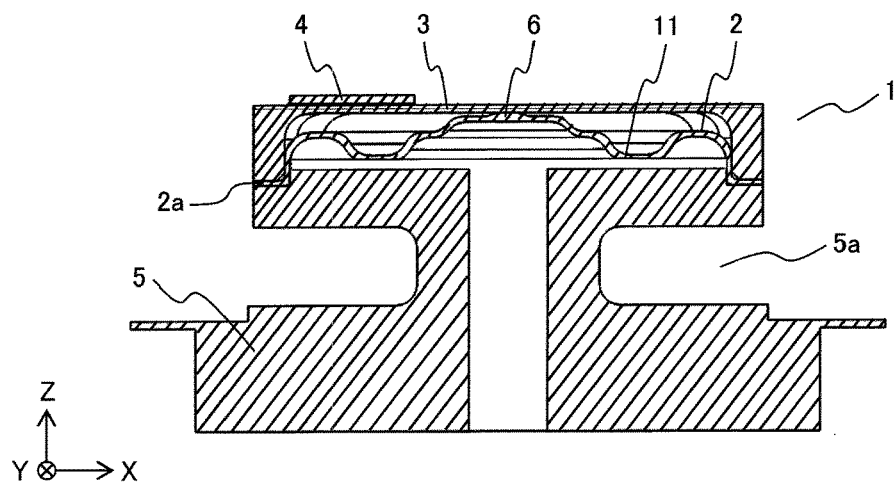
FIG. 11 is a sectional view taken on broken line A-A in FIG. 10.

A fifth embodiment of a pressure sensor according to the present invention is shown in FIGS. 10 and 11. In the fifth embodiment shown below, only points different from the first embodiment are explained.

In a pressure sensor 1 according to the present embodiment shown in the figures, a plurality of bends 11 are formed between the center part and the end of a diaphragm 2.

That is, in the pressure sensor 1 according to the present embodiment, slits 8A and 8B are formed in an elastic body 3 and penetrate the elastic body 3. Then in the X direction, the slits 8A and 8B are formed from an end to the other end of the elastic body 3 in length and are located at positions apart from a strain sensor 4 at a certain distance. The elastic body 3 over which the strain sensor 4 is arranged has the shape of a beam and the center and both the ends are fixed to the diaphragm 2.

Further, the diaphragm 2 is formed of a metal material, a stainless steel having a high corrosion resistance is used as the material, and the diaphragm 2 has a cylindrical shape and is configured so that: the thickness of the center part may be reduced so as to be thinner than the end part by working; and the center of the thinner center part of the diaphragm 2 may bulge partially in order to join to the elastic body 3. Moreover, the diaphragm 2 is structured so as to form a plurality of bends 11 between the outer periphery (end) and the center part (middle part) of the diaphragm 2.

By such a configuration according to the present embodiment, not only effects similar to the first embodiment can be obtained but also a plurality of bends 11 are formed between the outer periphery (end) and the center part (middle part) of the diaphragm 2 and stress concentration caused when pressure is applied by a fluid can be mitigated.

Sixth Embodiment

Figure 12:
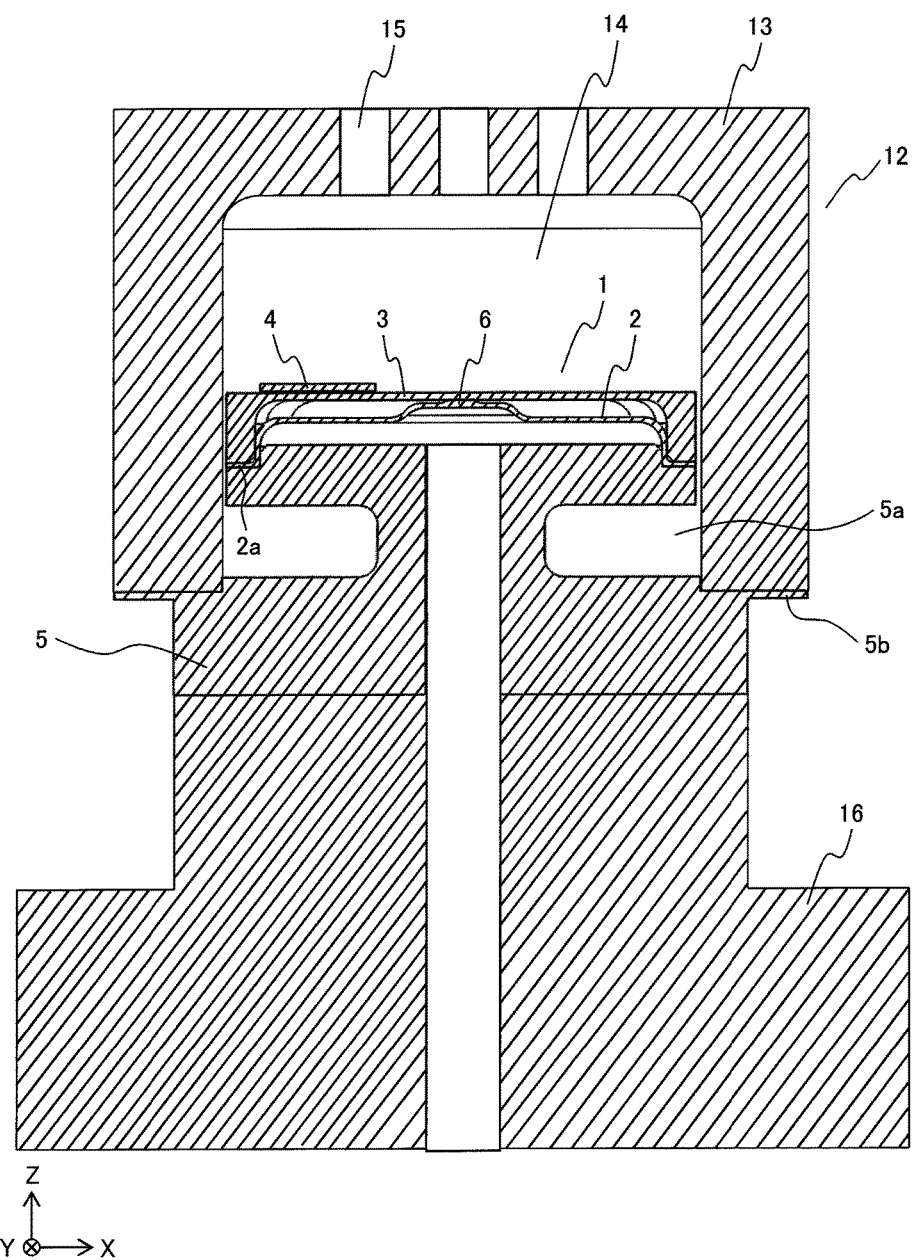
FIG. 12 is a sectional view showing an absolute pressure sensor according to a sixth embodiment of the present invention.

An absolute pressure sensor is shown in FIG. 12 as a sixth embodiment according to the present invention.

As shown in the figure, an absolute pressure sensor 12 according to the present embodiment includes a pressure sensor 1 configured similarly to the first embodiment stated above and an airtight housing 13. The airtight housing 13 is fixed to a support 5 in the manner of surrounding a diaphragm 2 and a strain sensor 4 and maintains an airtight space 14 around the strain sensor 4 to a constant atmospheric pressure.

For fixing the airtight housing 13 to the support 5, a fixing method capable of maintaining airtightness such as resistance welding or laser welding is used for example. By the method, a structure not affected by pressure variation other than a measurement object is obtained when an absolute pressure sensor 12 is used.

A brim 5b to be welded to the airtight housing 13 is provided at the outer periphery of the support 5 and the airtightness of the airtight space 14 is secured by fixing the brim 5b of the support 5 closely to the airtight housing 13. When a fixing method such as resistance welding or laser welding is used, a welded part is hardly formed during welding if the thickness of the brim 5b of the support 5 is too large and hence the thickness of the brim 5b is preferably not more than 0.20 mm. The thickness of the brim 5b is yet preferably not more than 0.15 mm. Meanwhile, if the thickness of the brim 5b is too small, the brim 5b is damaged by the influence of welding and the airtightness of the airtight space 14 cannot be secured and hence the thickness of the brim 5b is preferably not less than 0.10 mm.

When resistance welding or laser welding is applied to a brim 5b having a preferable thickness as stated above, since the thickness of the brim 5b is small, the airtightness of an airtight space 14 may not be secured undesirably as the result that a through hole is formed in the brim 5b by the impact of welding or the brim 5b breaks during the cooling after welding. To adopt a material in which foreign matters and defects such as voids are small as a material for forming a support 5 is desirable because such foreign matters and defects such as voids are inhibited from existing at the part of the brim 5b and there is no more fear that a through hole is formed in the brim 5b or the brim 5b breaks. A support 5 in which foreign matters and defects such as voids are small at a brim 5b can be manufactured by applying mechanical working to a material adopting a known technology such as a vacuum remelting method or a forging method for example.

When a forging method is selected as a method of reducing defects in a material for forming a support 5, it is desirable to manufacture the support 5 so that the direction of forged stream lines (direction of fiber) formed by forging may coincide with the in-plane direction of a brim 5b. Since a tensile strength in the direction of the forged stream lines is larger than those in other directions in a forged metal material, a brim 5b can be inhibited surely from braking during cooling after welding by making the direction of the forged stream lines coincide with the in-plane direction of the brim 5b. Meanwhile, the direction of forged stream lines in a support 5 can be identified easily by a method of polishing a cut plane of the support 5 and observing a metal texture by an optical microscope or the like or another method.

An output measured by the strain sensor 4 is taken out from a through electrode 15 formed in the airtight housing 13 to an exterior. The through electrode 15 is formed by plating and connected to the strain sensor 4 with a flexible substrate electrode (not shown in the figure) interposed and the airtightness of the airtight space 14 is secured.

Meanwhile, the support 5 is a member to support the connection between a flange 16 attached to a pipe in which a fluid as a measurement object flows and the diaphragm 2. The flange 16 is fixed to the pipe with a screw and sensitivity may change disadvantageously by the influence of the fastening of the screw if the flange 16 is fixed directly to the diaphragm 2.

To cope with that, a constriction 5*a* is formed at a part of the support 5 in order to mitigate a stress caused by screw fastening and transferred from the lower part of the support 5.

Even with an absolute pressure sensor of a configuration according to the present embodiment, effects similar to the first embodiment can be obtained.

Seventh Embodiment

Figure 13:
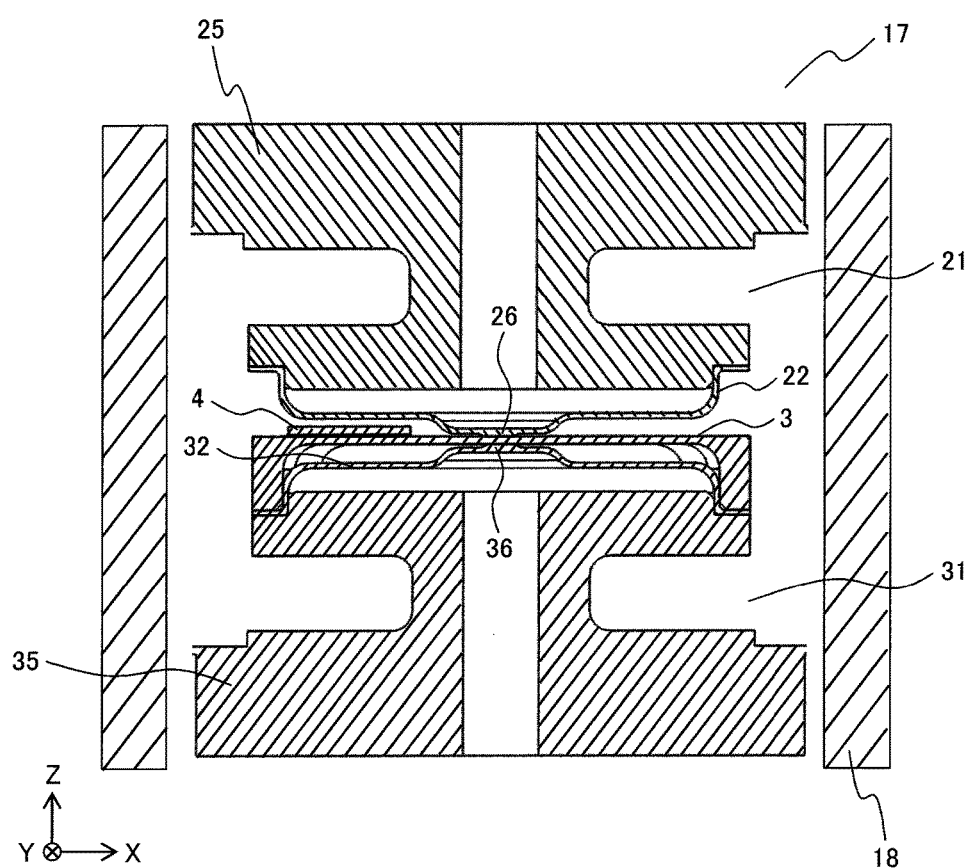
FIG. 13 is a sectional view showing a differential pressure sensor according to a seventh embodiment of the present invention.

A differential pressure sensor is shown in FIG. 13 as a seventh embodiment according to the present invention.

As shown in the figure, a differential pressure sensor 17 according to the present embodiment is generally configured so that: the differential pressure sensor 17 has a first diaphragm 22 and a second diaphragm 32 being arranged so as to face each other and deforming by the pressure of a fluid, an elastic body 3 being arranged between the first diaphragm 22 and the second diaphragm 32, joining to the first diaphragm 22 on one side, and joining to the second diaphragm 32 on the other side, and a strain sensor 4 being arranged on either one or the other side of the elastic body 3 and on the end side (left side in FIG. 13) apart from a position corresponding to the center of the first diaphragm 22 and the second diaphragm 32 and detecting deformation of the elastic body 3 working with the deformation of the first diaphragm 22 and the second diaphragm 32 as a strain; and the elastic body 3 is formed of a material having a linear expansion coefficient close to the linear expansion coefficient of a material constituting the strain sensor 4.

That is, the differential pressure sensor 17 according to the present embodiment includes two pressure sensors 21 and 31 having configurations similar to the first embodiment stated earlier and an airtight housing 18. A first diaphragm 22 and a second diaphragm 32 are arranged in the pressure sensors 21 and 31 respectively and fixed in the manner of facing each other with an elastic body 3 shared by the pressure sensors 21 and 31 interposed. Further, the airtight housing 18 surrounds the pressure sensors 21 and 31 and maintains an airtight space 14 around the pressure sensors 21 and 31 at a constant atmospheric pressure. As a result, a structure not influenced by pressure variation other than a measurement object is obtained.

Further, the first diaphragm 22 and the second diaphragm 32 are in contact with a first fluid and a second fluid respectively and are joined to the elastic body 3 at a joint 26 and a joint 36 respectively. The joint 26 and the joint 36 are fixed firmly by welding and the structure is constructed so that the first diaphragm 22 and the second diaphragm 32 may deform when difference in pressure is generated between the first fluid and the second fluid. A distortion is generated in the elastic body 3 in conjunction with the respective deformation of the first diaphragm 22 and the second diaphragm 32 and a differential pressure between the first fluid and the second fluid is measured by detecting the distortion with a strain sensor 4. The first fluid and the second fluid may be an identical fluid communicating with different places in an identical fluid system.

Even with a differential pressure sensor of a configuration according to the present embodiment, effects similar to the first embodiment can be obtained.

Further, a pressure sensor 1 or a differential pressure sensor 17 according to the present invention can be used in application for monitoring a pressure of an evaluation object by being incorporated into a mass flow controller used in a semiconductor manufacturing apparatus for example.

Meanwhile, the present invention is not limited to the above embodiments and includes various modifications. For example, the above embodiments are explained in detail for making the present invention easy to be understood and the present invention is not necessarily limited to embodiments having all the explained configurations. Further, it is possible to: replace a part of the configuration of an embodiment with the configuration of another embodiment; and also add the configuration of an embodiment to the configuration of another embodiment. Moreover, a part of the configuration of each of the embodiments can be added to, deleted from, or replaced with another configuration.

REFERENCE SIGNS LIST

1, 21, 31 Pressure sensor
2 Diaphragm
2*a* Brim of diaphragm
3 Elastic body
4 Strain sensor
5, 25, 35 Support
5*a* Constriction of support
5*b* Brim
6, 26, 36 Joint
7*a*, 7*b*, 7*c*, 7*d* Strain gauge
8A, 8B Slit
9A First through hole
9B Second through hole
10A, 10B Recess (concavity)
11 Bend
12 Absolute pressure sensor
13, 18 Airtight housing
14 Airtight space
15 Through electrode
16 Flange
17 Differential pressure sensor
22 First diaphragm
32 Second diaphragm

The invention claimed is:

1. A pressure sensor comprising:
   a diaphragm deforming by a pressure of a fluid;
   an elastic body covering the whole surface of the diaphragm and joining to the diaphragm on one side; and
   a strain sensor being arranged by joining on the other side of the elastic body and on an end side apart from a position corresponding to a center of the diaphragm and detecting a deformation of the elastic body working together with a deformation of the diaphragm as a strain,
   wherein the elastic body is formed of a material having a linear expansion coefficient close to the linear expansion coefficient of a material constituting the strain sensor.

2. A pressure sensor according to claim 1,
   wherein the diaphragm is formed of a stainless steel or a clad material including the stainless steel and another metal material.

3. A pressure sensor according to claim 1,
   wherein the diaphragm has a cylindrical shape and is configured so that a center part is thinner than an end part, a center of the thinner center part bulges, and the bulging part joins to the elastic body.

4. A pressure sensor according to claim 3,
   wherein: the strain sensor includes silicon; and the elastic body includes any one of a kovar alloy, a 42 alloy, and an invar alloy, each of which has a linear expansion coefficient close to the linear expansion coefficient of the silicon.

5. A pressure sensor according to claim 4, wherein the elastic body has a cylindrical shape and is configured so that a center part is thinner than an end part and a hole is formed at a part other than a part where the strain sensor is arranged in the elastic body.

6. A pressure sensor according to claim 5, wherein: the hole includes two slits being formed in a manner of interposing the strain sensor and extending from an end to the other end of the elastic body; and the slits penetrate the elastic body.

7. A pressure sensor according to claim 5, wherein the hole includes: a first through hole being formed in a manner of interposing the strain sensor and penetrating the elastic body; and a second through hole communicating with the first through hole and being formed in the elastic body on the side opposite to the side where the strain sensor is arranged.

8. A pressure sensor according to claim 5, wherein: the hole includes two recesses (concavities) being formed in a manner of interposing the strain sensor and extending from an end to the other end of the elastic body; and the recesses do not penetrate the elastic body.

9. A pressure sensor according to claim 6, wherein the elastic body has a width equal to or larger than a size of the strain sensor and joins at least to two sites of a center part and an outer periphery of the diaphragm.

10. A pressure sensor according to claim 9, wherein the elastic body joins to the center part of the diaphragm at one point and to the outer periphery of the diaphragm around the whole circumference.

11. A pressure sensor according to claim 10, wherein the elastic body joins to the strain sensor with a metal or a low-melting-point glass.

12. A pressure sensor according to claim 11, wherein the metal for joining the elastic body to the strain sensor is Au/Sn or Au/Ge.

13. A pressure sensor according to claim 11, wherein the low-melting-point glass for joining the elastic body to the strain sensor is a vanadium-based glass.

14. A pressure sensor according to claim 13, wherein the diaphragm has a plurality of bends between a center part of the diaphragm and an end.

15. A pressure sensor according to claim 1, wherein:
the pressure sensor has a support fixing an outer periphery of the diaphragm and an airtight housing fixed to the support and arranged in a manner of surrounding the diaphragm, the elastic body, and the strain sensor; and
the support and the airtight housing are fixed so as to retain airtightness.

16. A pressure sensor according to claim 15, wherein a brim is formed at the outer periphery of the support, the airtight housing is fixed to the brim, and the thickness of the brim is 0.10 mm to 0.20 mm.

17. A pressure sensor according to claim 16, wherein the support is formed of a forged material and a direction of forged stream lines formed by forging coincides with an in-plane direction of the brim.

18. A differential pressure sensor comprising:
a first diaphragm and a second diaphragm which are arranged so as to face each other and deforming by a pressure of a fluid;
an elastic body being arranged between the first diaphragm and the second diaphragm and joining to the first diaphragm on one side and the second diaphragm on the other side; and
a strain sensor being arranged on one side or the other side of the elastic body and on an end side apart from a position corresponding to a center of the first diaphragm and the second diaphragm and detecting a deformation of the elastic body working together with a deformation of the first diaphragm and the second diaphragm as a strain; and
wherein the elastic body is formed of a material having a linear expansion coefficient close to the linear expansion coefficient of a material constituting the strain sensor.

19. A mass flow controller which monitors the pressure of a fluid,
the mass flow controller comprising a pressure sensor according to claim 14.

20. A mass flow controller which monitors the pressure of a fluid,
the mass flow controller comprising a differential pressure sensor according to claim 18.

* * * * *